United States Patent
Sakano et al.

(10) Patent No.: US 7,968,741 B2
(45) Date of Patent: Jun. 28, 2011

(54) METHOD OF PREPARING DISILANOL COMPOUND AND METHOD OF STORING DISILANOL COMPOUND

(75) Inventors: Yasunori Sakano, Annaka (JP); Takashi Matsuda, Annaka (JP); Noriyuki Koike, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/826,940

(22) Filed: Jul. 19, 2007

(65) Prior Publication Data

US 2008/0021233 A1    Jan. 24, 2008

(30) Foreign Application Priority Data

Jul. 21, 2006   (JP) ................. 2006-199782

(51) Int. Cl.
   *C07F 7/08*    (2006.01)
(52) U.S. Cl. ........ 556/471; 556/413; 556/427; 556/435; 556/465
(58) Field of Classification Search ........................ None
   See application file for complete search history.

(56) References Cited

U.S. PATENT DOCUMENTS

| | | |
|---|---|---|
| 3,099,640 A | 7/1963 | Hay |
| 3,627,801 A * | 12/1971 | Pierce et al. ................ 556/431 |
| 5,286,891 A | 2/1994 | Tabei et al. |
| 5,705,591 A | 1/1998 | Matsuda et al. |
| 6,252,029 B1 | 6/2001 | Amako et al. |
| 2005/0090606 A1 | 4/2005 | Belin et al. |

FOREIGN PATENT DOCUMENTS

| | | |
|---|---|---|
| DE | 1 158 070 | 11/1963 |
| GB | 1252147 A | 11/1971 |
| JP | 46-002094 Y1 | 1/1971 |
| JP | 60-23385 A | 2/1985 |
| JP | 5-194748 A | 8/1993 |
| JP | 9-077777 A | 3/1997 |
| JP | 11-292884 A | 10/1999 |
| JP | 2000-226413 A | 8/2000 |

OTHER PUBLICATIONS

Chizhova et al., Russian Chemical Bulletin, International Edition, vol. 49, No. 8, pp. 1436-1441, Aug. 2000, XP009091977.

Noll et al., "Chemie und Technologie der Silicone," 1968, Verlag Chemie, Weinheim, XP002457943, p. 84.

* cited by examiner

*Primary Examiner* — Daniel M Sullivan
*Assistant Examiner* — Yevegeny Valenrod
(74) *Attorney, Agent, or Firm* — Birch, Stewart, Kolasch & Birch, LLP

(57) ABSTRACT

A method of preparing a disilanol compound by hydrolyzing a dichlorosilane compound having Si—Cl bonds at both ends, characterized in that the method comprises the step of hydrolyzing the dichlorosilane compound in the presence of a tertiary amine compound.

13 Claims, 2 Drawing Sheets

METHOD OF PREPARING DISILANOL COMPOUND AND METHOD OF STORING DISILANOL COMPOUND

CROSS REFERENCE

This application claims benefit of Japanese Patent application No. 2006-199782 filed on Jul. 21, 2006, the contents of which are hereby incorporated by reference.

FIELD OF THE INVENTION

The present invention relates to a method of preparing a fluorine-containing organic silicon compound having silanol groups at both ends and a method of storing the same. The silicon compound is useful as a base polymer for a rubber composition which is cured via a condensation reaction.

DESCRIPTION OF THE PRIOR ART

There are some known methods of preparing a silanol compound, i.e., Si—OH bond-containing compound, from an organochlorosilane, i.e., Si—Cl bond-containing compound. For example, a hydrolysis of a mixture of triorganochlorosilane and hexaorganodisilazane at a pH of from 6 to 9 is known from Japanese Patent Publication of Examined Application No. S46-8690, and a hydrolysis of a mixture of triorganochlorosilane and hexaorganodisilazane without using a pH adjusting agent is known from Japanese Patent Publication of Examined Application No. S62-57188. These methods are useful for preparing a relatively low molecular weight silanol compound of which separation, aqueous cleaning, and distillation are relatively easy, but are not so useful for preparing a high molecular weight or polymeric silanol.

As a method applicable to a high molecular weight or polymeric disilanol, a method comprising the step of dropping a chlorosilane compound in a mixture of an epoxide compound such as propylene oxide and water is known from Japanese Patent Application Laid-Open No. H11-292884. A drawback of the method is that a conversion rate from —Cl to —OH cannot be higher than 70 or 80% for the reason that the chlorosilane also reacts with a byproduct alcohol which is formed by the reaction of propylene oxide with hydrogen chloride formed by the hydrolysis.

A method, which can attain a conversion rate of 90% or higher, is known from Japanese Patent Application Laid-Open No. 2000-226413. In the method, an organosilicon compound having chlorine atoms at both ends is reacted with acetic acid anhydride to have $CH_3COO$ groups at both ends, which are then hydrolyzed. A drawback of the method is that acetic acid formed in the reaction catalyses condensation reaction of silanol compound itself, causing formation of a condensation product of the silanol compounds. Moreover, residual acetic acid, which is not removed by a purification process, causes to from a condensation product during storing the silanol.

SUMMARY OF THE INVENTION

An object of the present invention is to provide a method of preparing disilanol compound having Si—OH at both ends with a high conversion rate, and a method of storing a disilanol compound.

One aspect of the present invention is a method of preparing a disilanol compound by hydrolyzing a dichlorosilane compound having Si—Cl bonds at both ends, characterized in that the method comprises the step of hydrolyzing the dichlorosilane compound in the presence of a tertiary amine compound.

Another aspect of the present invention is a method of storing a fluorine-containing disilanol compound represented by the following formula (3) in the presence of a tertiary amine in such an amount that a molar ratio of the tertiary amine to a silanol group of the fluorine-containing disilanol compound ranges from 0.001 to 20, $$HO-Z-R^1-R_f-R^1-Z-OH \quad (3)$$

wherein $R_f$ is a divalent fluorinated hydrocarbon group or a divalent fluorinated polyether group, $R^1$ may be the same with or different from each other and is a substituted or unsubstituted divalent hydrocarbon group which may have at least one atom selected from the group consisting of oxygen, nitrogen, silicon, and sulfur atoms, and Z is a group represented by the following formula (2)

$$-SiR^2R^3- \quad (2)$$

wherein $R^2$ and $R^3$ may be the same with or different from each other and are monovalent organic groups.

The method of the present invention can attain a conversion rate of 90% or higher. The storing method of the present invention enables one to store a disilanol compound without causing condensation reaction of the disilanol compound.

DESCRIPTION OF THE PREFERRED EMBODIMENTS

Figure 1:
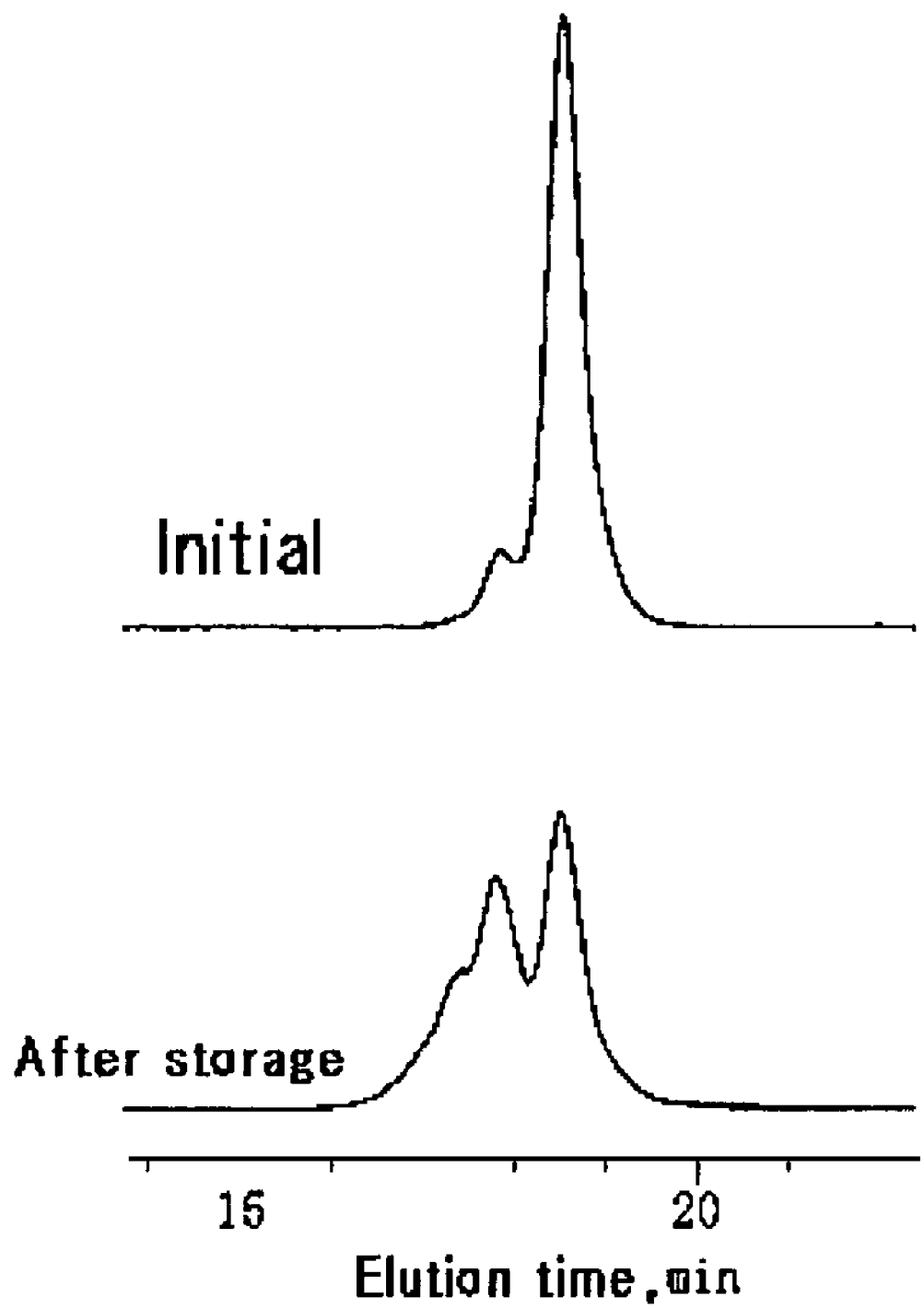
FIG. 1 is a GPC chromatogram showing an increase of condensed disilanol during storage.

The present method is characterized by the use of a tertiary amine compound in the step of hydrolyzing dichlorosilane. A tertiary amine compound is known to trap hydrogen chloride formed in a reaction from Published International Application No. 2005-522515, for instance. However, it is not known that, by using a tertiary amine compound in preparing disilanol compound, a higher conversion rate than the aforesaid epoxide compound, can be attained. Further, it cannot be expectable from prior art that a tertiary amine compound prevents condensation of disilanol compound to attain stable storage of the disilanol compound.

As the tertiary amine, those that can trap hydrogen chloride are used. Preferably, the tertiary amine represented by the following formula (4) is used:

$$R^4-[N(R^5)-Q]_a-R^6 \quad (4)$$

wherein $R^4$ is a $C_{1-20}$ monovalent hydrocarbon group which may have an ether bond, $R^5$ may be the same with or different from each other and is a $C_{1-20}$ monovalent hydrocarbon group which may have an ether bond, $R^6$ is a hydrogen atom or a $C_{1-20}$ monovalent hydrocarbon group which may have an ether bond, at least two of $R^4$, $R^5$ and $R^6$ may be bonded together to form a ring, Q may be the same with or different from each other and is a $C_{1-20}$ divalent hydrocarbon group which may have an ether bond, and a is an integer of from 1 to 10.

Examples of $C_{1-20}$ monovalent hydrocarbon group include alkyl groups such as methyl, ethyl, propyl, isopropyl, butyl, isobutyl, tert-butyl, pentyl, neopentyl, hexyl, heptyl, octyl, nonyl, and decyl groups; cycloalkyl groups such as cyclopentyl, cyclohexyl, and cycloheptyl groups; aryl groups such as phenyl, tolyl, xylyl, and naphthyl groups; and aralkyl groups such as benzyl, phenylethyl, and phenylpropyl groups.

Examples of Q include alkylene groups such as methylene, ethylene, propylene, iropropylene, butylene, and hexamethylene groups; cycloalkylene group such as a cyclohexylene group; and arylene groups such as phenylene, tolylene, xylylene, naphthylene and biphenylene group. These groups may have an ether bond. Among these, preferred are those represented by the following formulas:

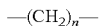

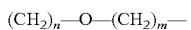

wherein each of n and m is an integer of from 1 to 8.

In the formula (4), a is an integer of from 1 to 20, preferably from 1 to 6. When a is 2 or larger, $R^5$ and Q may be different among 2 or more of $[N(R^5)$-Q] units. At least two of $R^4$, $R^5$ and $R^6$ may be bonded to from a ring. Examples of the ring structure are those listed for Q.

Examples of preferred tertiary amine compound include triethylamine, tripropylamine, tributylamine, trihexylamine, trioctylamine, tetraethyl-ethylenediamine, pentaethyl-diethylene triamine, hexamethyl-triethylenetetramine; pyperadine derivatives such as 1,4-dimethylpyperadine; morphorine derivatives such as N-methylmorphorine; 1-azabicyclo[2,2,2]octane, 1,4-diazabicyclo[2,2,2]octane; aniline derivatives such as N,N-dimethylaniline, and a mixture of these amines. Among these, triethylamine and tributylamine are more preferred. When the present method is combined with the aftermentioned storing method of the present invention, a combinatory use of a tertiary amine having low boiling point such as triethylamine and the one having higher boiling point such as tri-n-butylamine is very advantageous.

The dichlorosilane compound represented by the following formula is preferred, hereinafter referred to as dichlorosilane compound (1):

$$\text{Cl}-Z-R^1-R_f-R^1-Z-\text{Cl} \quad (1)$$

wherein $R_f$ is a divalent fluorinated hydrocarbon group or a divalent fluorinated polyether group. Examples of the fluorinated hydrocarbon group include linear and branched fluorinated alkylene groups having 1 to 6, preferably 4 to 6, carbon atoms, for example, —$C_4F_8$— and —$C_6F_{12}$—.

Examples of the divalent fluorinated polyether group are as shown below:

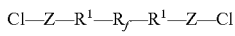

wherein each of m and n is an integer of from 1 to 100, provided that an average of m+n ranges from 5 to 150;

—$CF_2CF_2OC_4F_8OCF_2CF_2$—

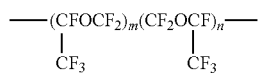

—$CF_2(OCF_2CF_2)_n(OCF_2)_mOCF_2$— wherein n is an integer of from 2 to 100 with an average thereof ranging from 5 to 50, and m is an integer of from 1 to 20 with an average thereof ranges from 1 to 10;

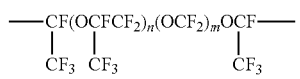

wherein n is an integer of from 2 to 100 with an average thereof ranging from 5 to 50, and m is an integer of from 1 to 20 with an average thereof ranges from 1 to 10;

—$CF_2CF_2(OCF_2CF_2CF_2)_nOCF_2CF_2$— wherein n is an integer of from 2 to 200 with an average thereof ranging from 5 to 100;

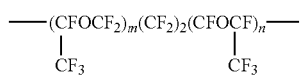

wherein each of m and n is an integer of from 1 to 100, provided that an average of m+n ranges from 5 to 150.

In the formula (1), $R^1$ may be the same with or different from each other and is a substituted or unsubstituted divalent hydrocarbon group which may have at least one atom selected from the group consisting of oxygen, nitrogen, silicon, and sulfur atoms. Preferably, $R^1$ is a $C_{2-20}$ group, for example, an alkyl group such as ethylene, propylene, isopropylene, butylene, or hexamethylene group; a cycloalkylene group such as a cyclohexylene group; an arylene group such as a phenylene, tolylene, xylylene, naphthylene, or biphenylene group; an alkarylene group; or partly or wholly halogenated group thereof.

In $R^1$, an oxygen atom may exist as —O—; a nitrogen atom may exist in —NR—, wherein R is a hydrogen atom or a $C_{1-10}$ alkyl or aryl group, or as —N=; a silicon atom may exist in —SiR'R"—, wherein each of R' and R" is a $C_{1-10}$ alkyl or aryl group; a sulfur atom exists as —S—; oxygen and nitrogen atoms may exist in an amide group, —CONR, wherein R is as defined above; and oxygen, nitrogen and sulfur atoms may exist in a sulfonamide group or —$SO_2$NR, wherein R is as defined above.

Examples of $R^1$ are as shown below, wherein Me represents a methyl group and Ph a phenyl group. In each formula, the bond at the left side is bound to Rf and the one at the right side is bound to Z in the formula (1).

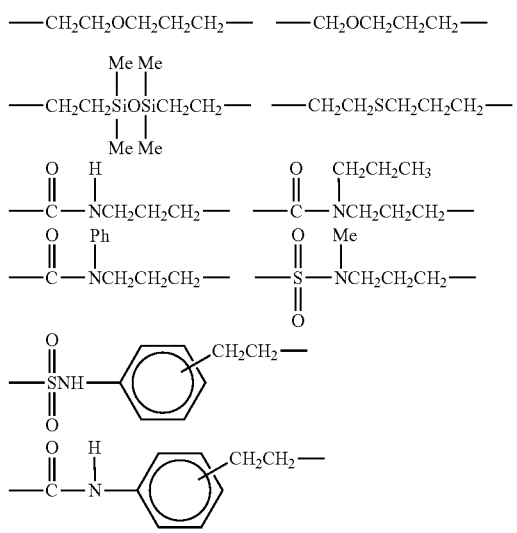

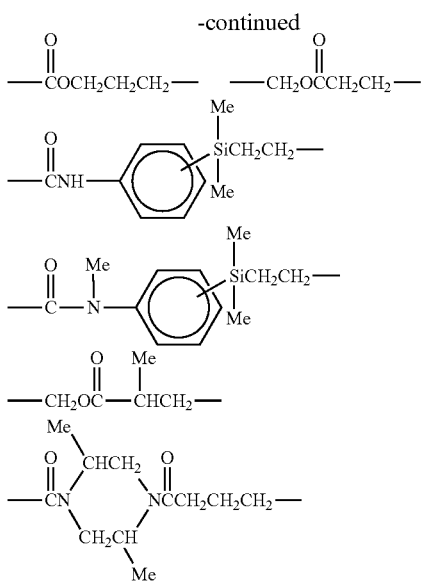

In the formula (1), Z is a group represented by the following formula (2):

$$-SiR^2R^3- \quad (2)$$

wherein $R^2$ and $R^3$ may be the same with or different from each other and are monovalent organic groups. Preferably, $R^2$ and $R^3$ are $C_{1-12}$ hydrocarbon groups, for example, alkyl groups such as methyl, ethyl, propyl, isopropyl, butyl, isobutyl, tert-butyl, pentyl, neopentyl, hexyl, heptyl, octyl, nonyl, and decyl groups; cycloalkyl groups such as cyclopentyl, cyclohexyl, and cycloheptyl groups; aryl groups such as phenyl, tolyl, xylyl, and naphthyl groups; aralkyl groups such as benzyl, phenylethyl, and phenylpropyl groups; and partly or wholly halogenated groups thereof such as chloromethyl, bromoethyl, chloropropyl, trifluoropropyl, and 3,3,4,4,5,5,6,6,6-nonafluorohexyl groups, among which a methyl group is preferred.

In the hydrolysis reaction of the dichloro compound (1), an amount of each the dichloro compound (1), tertiary amine, and water is adjusted according to a molar amount of the Si—Cl bond contained in the dichloro compound (1). Water is used in such an amount that a molar ratio thereof to the Si—Cl bond contained in the dichloro compound (1) is at least one, preferably at least two. A molar ratio of the tertiary amine to the Si—Cl bond is at least 0.1, preferably at least 2. There is no upper limit of the amount and 50-time molar amount may be used as a solvent.

The hydrolysis reaction may be performed according to known procedures. Preferably, to prevent a condensation reaction between unreacted dichloro compound (1) and disilanol formed, the dichloro compound (1) is gradually added to a mixture of water and the tertiary amine, or water is added to a mixture of dichloro compound (1) and the tertiary amine which has been well mixed in advance.

A reaction mixture may be diluted with an organic solvent in an amount not to adversely affect the hydrolysis reaction. The use of an organic solvent is advantageous to promote the reaction when the solvent dissolves each reactant and reaction product to form an uniform solution. When such solvent is used, each component, that is, water, the tertiary amine, the compound (1), or a mixture thereof may be dissolved in advance with the same or different organic solvent. Examples of the organic solvent include hydrocarbon solvents such as n-hexane, cyclohexane, toluene, petroleum ether, and xylene; ether solvents such as diethyl ether, n-butyl ether, ethylene glycol dimethyl ether, dioxane, and tetrahydrofuran; ketone solvents such as acetone, methyl ethyl ketone, dibutyl ketone, and ethyl acetate; chlorinated hydrocarbon solvents such as methylene chloride, chlorobenzene, and chloroform; and fluorinated solvents such as trifluorobenzene, 1,3-bistrifluoromethylbenzene and fluoroalkyl ether; and a mixture thereof.

The reaction is performed preferably at a temperature of from 1 to 70° C. typically for 1 to 24 hours.

Hydrogen chloride formed and a salt of hydrogen chloride with a tertiary amine can be removed by washing reaction mixture with water or treating the reaction mixture with an adsorbent after the reaction. Preferably, a carbonate salt or a hydrogen carbonate salt of an alkali metal and/or alkali earth metal, or a mixture thereof, hereinafter collectively referred to as carbonate salt, is added to the reaction mixture, and then water is removed. Subsequently, solid materials including the carbonate salt are removed by filtration.

Examples of preferred carbonate salt include sodium hydrogen carbonate, potassium hydrogen carbonate, magnesium hydrogen carbonate, calcium carbonate, and magnesium carbonate.

The carbonate salt of alkali metal may be used in such an amount that a molar ratio of the carbonate salt to the Si—Cl bond contained in the dichloro compound (1) ranges from 0.55 to 10, preferably from 1.1 to 3, and the carbonate salt of alkali earth metal may be used in such an amount that a molar ratio of the carbonate salt to the Si—Cl bond contained in the dichloro compound (1) ranges from 1.1 to 20, preferably from 2 to 5. The carbonate salt may be added in the form of powder to a reaction mixture resulting from the hydrolysis reaction and thoroughly mixed. The mixing may be performed at a temperature of from 1 to 100° C. for a period of time, though it varies depending on a size of the powder and mixing efficiency, of 6 hours at room temperature, or of about 1 hour at 90° C. Subsequently, water and unreacted tertiary amine are removed by phase separation and/or vacuum distillation and then solid materials are removed by filtration.

In the filtration step, an organic solvent may be added to a reaction mixture to dilute the mixture and then removed from the filtrate. Preferred examples of the organic solvent are fluorinated solvents such as trifluorobenzene, 1,3-bistrifluoromethylbenzene, fluoroalkyl ether and a mixture thereof. These solvents can be removed by vacuum distillation at a temperature of from 60 to 120° C.

Simultaneously with or after the filtration, the filtrate containing the reaction product may be treated with a purification means, for example, a dehydrating agent such as sodium sulfate, magnesium sulfate or molecular sieve; an adsorbent for adsorbing inorganic or organic impurities such as active carbon, activated earth, alumina, or polymeric adsorbent.

By the aforesaid procedures, a fluorine-containing disilanol compound can be obtained with a ratio of conversion from Si—Cl to Si—OH of 90% or higher.

The present invention also provides a method of storing a fluorine-containing disilanol compound of the formula (3), hereinafter referred to as disilanol compound (3), in the presence of a tertiary amine compound in such an amount that a molar ratio of the tertiary amine to the silanol group ranges from 0.001 to 20, preferably from 0.005 to 0.2. The tertiary amine compound prevents condensation reaction among the disilanol compound molecules when there is residual or contaminant acidic materials, particularly hydrogen chloride.

Preferred tertiary amines are those having a boiling point of 100° C. or higher such as tripropylamine, tributylamine, trihexylamine, and trioctylamine.

The aforesaid storing method can be used not only for storing a disilanol compound prepared by the method of present invention but also those prepared by other methods, for example, those described in Japanese Patent Application Laid-Open No. H11-292884 and Japanese Patent Application Laid-Open No. 2000-226413.

Combination of the storing method with the preparation method of the present invention is very advantageous. Particularly, by using a mixture of a tertiary amine having a boiling point low enough to be removed by vacuum distillation, for example, triethylamine of which boiling point is 98° C., with another tertiary amine having a high boiling point such as tri-n-butylamine of which boiling point is 216° C., the hydrolysis is performed in the presence of both tertiary amines and tri-n-butylamine remains in the reaction product.

EXAMPLES

The present invention will be explained with reference to the following Examples, but not limited thereto.

Example 1

In a one-liter four-necked flask equipped with a stirring rod and a thermometer, were placed 20 g of water, 20 g of triethylamine, and 40 g of 1,3-bistrifluoromethylbenzene and cooled to 5 ° C. The mixture was stirred while maintaining the temperature at 5 ° C. In a 500-ml dropping funnel, were placed 300 g of the compound represented by the following formula (5) and 150 g of 1,3-bistrifluoromethylbenzene, and the inlet of the funnel was sealed with nitrogen gas. Then, the mixture of the compound of the formula (5) and 1,3-bistrifluoromethylbenzene was dropped in the four-necked flask while maintaining a temperature of the contents of the four-necked flask at a temperature of from 5 to 10° C.

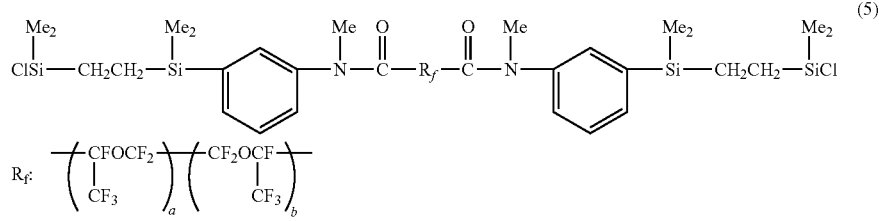

In the formula (5), a and b are integers of 1 or larger with an average of a+b is 90.

After completing the dropping, the reaction mixture in the flask was stirred at room temperature for 2 hours, to which 6.0 g of sodium carbonate was added and stirred for additional one hour. Subsequently, a Dimroth was attached to the flask and then the reaction mixture was heated at a temperature of 90° C. for 2 hours while stirring. After cooling the reaction mixture to room temperature, water, triethylamine and 1,3-bistrifluoromethylbenzen were removed by vacuum distillation at a temperature of 80° C. and a pressure of 2 mm Hg with an evaporator. The distillation residue was cooled to room temperature, to which were added 150 g of 1,3-bistrifluoromethylbenzen and 6 g of active carbon, which were stirred for 2 hours and then subjected to pressure filtration using a filter plate. The filtrate obtained was subjected to vacuum distillation at a temperature of 80° C. and a pressure of 2 mm Hg to obtain 276 g of colorless transparent liquid compound.

The compound was found to have the following structure of the formula (6), wherein $R_f$ is as defined above, by $^1$H-NMR analysis.

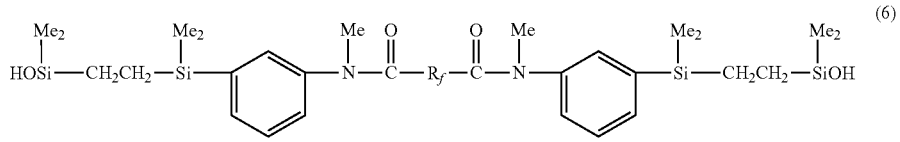

$^1$H-NMR peaks observed are as follows:
δ0.05 (s, HO—Si—CH$_3$)
δ0.30 (s, arom-Si—CH$_3$)
δ0.45 (m, HO—Si—CH$_2$)
δ0.70 (m, arom-Si—CH$_2$)
δ1.70 (s, Si—OH)
δ3.30 (s, N—CH$_3$)
δ7.1-7.5 (m, arom)

A ratio of conversion to Si—OH was 94% which was calculated from an amount of Si—OH determined from an integrated peak ratio of $^1$H of Si—OH to that of N—CH$_3$.

Example 2

In a one-liter four-necked flask equipped with a stirring rod and a thermometer, were placed 20 g of triethylamine, 200 g of 1,3-bistrifluoromethylbenzene and 300 g of the compound of the aforesaid formula (5) and stirred at room temperature for 30 minutes. The mixture obtained was cooled to 3° C. To the mixture, 20 g of water was added via a funnel placed at the neck on top of the flask while stirring the mixture thoroughly. The addition of water caused an increase in a temperature of the reaction mixture in the flask to 9° C. At that temperature, the reaction mixture was stirred for 30 minutes. Then, the cooling was stopped, and the temperature of the reaction mixture was allowed to rise to room temperature. Subsequently, 6.0 g of calcium carbonate was added ro the reaction mixture and stirred for 1 hour. Then, a Dimroth was attached to the flask and the reaction mixture was heated at a temperature of 90° C. for 2 hours while stirring. After cooling the reaction mixture to room temperature, water, triethylamine and 1,3-bistrifluoromethylbenzen were removed by vacuum distillation at a temperature of 80° C. and a pressure of 2 mm Hg with an evaporator. The distillation residue was cooled to room temperature, to which were added 150 g of 1,3-bistrifluoromethylbenzen and 6 g of active carbon. After stirring for 2 hours, the mixture was subjected to pressure filtration using a filter plate. The filtrate obtained was subjected to vacuum distillation at a temperature of 80° C. and a pressure of 2 mm Hg to obtain 273 g of the compound represented by the formula (6) with a conversion ratio of 93% calculated as in Example 1.

Comparative Example 1

Using the method described in Japanese Patent Application Laid-Open No. 2000-226413, 184 g of the compound of the formula (6) was prepared from 200 g of the compound of the formula (5) with a conversion ratio of 93% calculated as in Example 1.

Example 3

To 100 g of the compound of the formula (6) prepared in Example 1, 0.5 g of tri-n-butylamine was added and stirred for 1 hour.

Example 4

To 100 g of the compound of the formula (6) prepared in Example 1, 0.5 g of tri-n-butylamine was added and stirred for 1 hour.

Example 5

The procedures of Example 1 were repeated except that 2 g of tri-n-octylamine was added in place of 20 g of triethylamine. The compound of the formula (6) in an amount of 271 g was obtained with a conversion ratio of 94% calculated as in Example 1.

Storage Stability

Each sample prepared in Examples 1-5 and Comparative Example 1 was analyzed immediately after prepared, after kept at 70° C. in a closed container for 7 days, and 21 days by Gel permeation chromatography under the following conditions.

Column: TSK-GEL MultiporeHXL×2, ex Toyo soda
Eluent: Asahi Clean AK225, ex Asahi Glass Co., Ltd.
Column temperature: 35° C.
Flow rate: 1 ml/min
Detector: Evaporative Light Scattering Detector DDL-31, ex Eurosep Instrument Co.
Detector temperature: 45° C.

Figure 2:
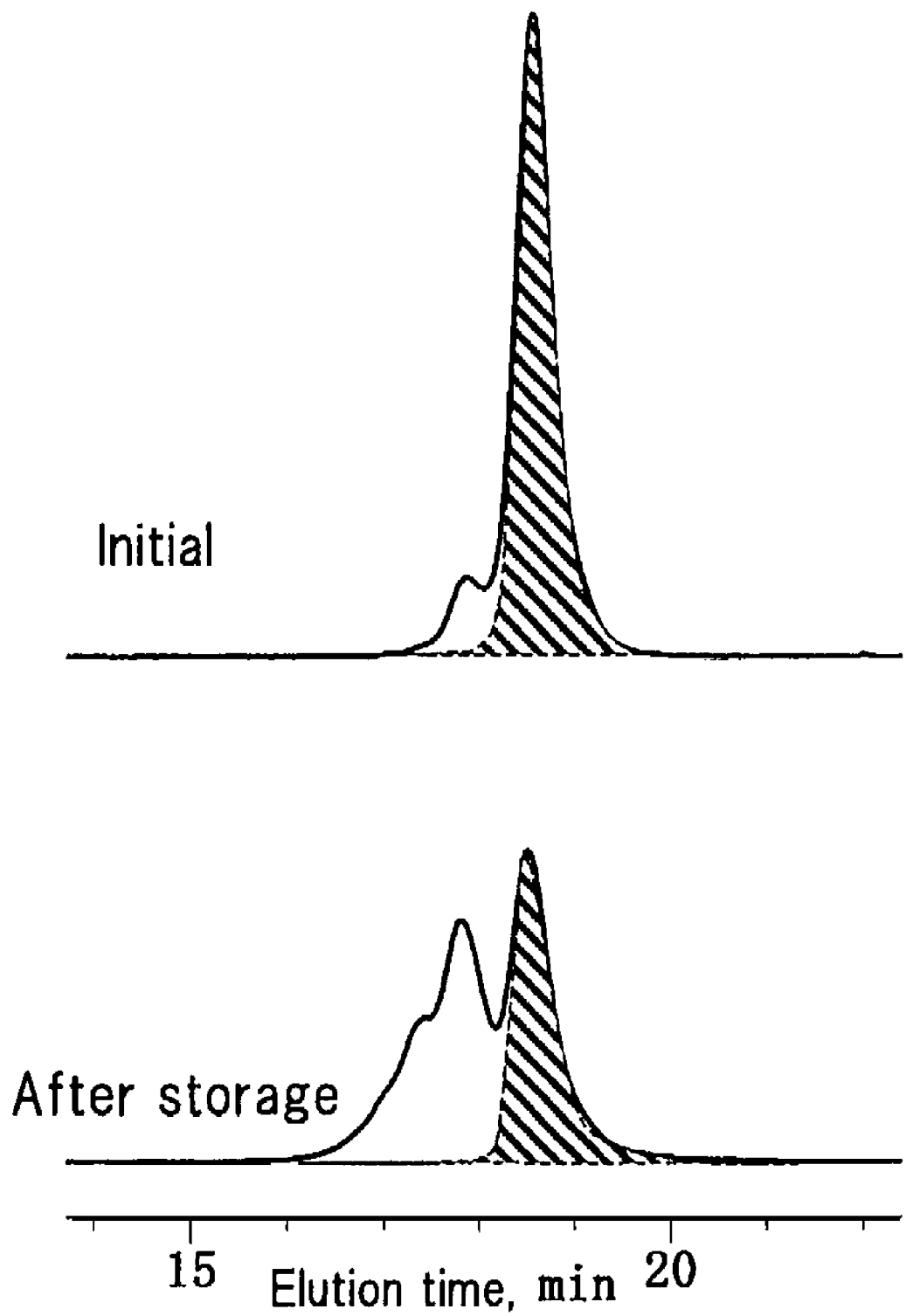
FIG. 2 is a GPC chromatogram showing shaded peak of a yet-uncondensed disilanol.

FIG. 1 shows GPC chromatograms of a disilanol compound before (upper one) and after (lower one) storage at an elevated temperature. As can be seen from the chromatograms, peaks in higher molecular weight region increase with storage time. Therefore, a change in an area ratio of peak of the low molecular weight disilanol, hereinafter referred to yet-uncondensed disilanol, was used as an index of storage stability. A ratio of yet-uncondensed disilanol was calculated from the following equation wherein the shaded part is as shown in FIG. 2.

A ratio of the yet-uncondensed disilanol (R)=an area of shaded peak (S')/a total peak area (S)

Using an initial ratio of the yet-uncondensed disilanol (R $_{initial}$) and the one determined after the storage (R after storage), a preservation percentage of the ratio was calculated according to the following equation.

A preservation percentage of the ratio of the yet-uncondensed disilanol $(r)=(R_{after\ storage}/R_{initial})\times 100(\%)$ The results are as shown in Table 1.

TABLE 1

| | Preservation (%) of yet-uncondensed disilanol after storing at 70° C. in a closed container | | | | | |
|---|---|---|---|---|---|---|
| | Example 1 | Example 2 | Example 3 | Example 4 | Example 5 | Comparative Example 1 |
| 7 days (%) | 95 | 96 | 100 | 97 | 98 | 61 |
| 21 days (%) | 81 | 83 | 100 | 88 | 94 | 0 |

As shown in Table 1, the disilanol compound prepared in Comparative Example 1 condensed significantly even in 7 days. In contrast, over 80% of the disilanol compound prepared by the present method remained uncondensed. In Examples 3-5 where the disilanol compound was stored in the presence of the tertiary amine, about 90% or more of the disilanol compound remained uncondensed. In Example 5, tri-n-octylamine worked both in the preparation process and the storage process.

As described above, the present preparation method enables one to prepare a disilanol compound with a high yield. The present storing method allows stable storage of a disilanol compound for a prolonged period of time. It is very advantageous to store a disilanol compound prepared by the present method with the tertiary amine used in the preparation being remained.

The invention claimed is:

1. A method of preparing a disilanol compound by hydrolyzing a dichlorosilane compound having Si—Cl bonds at both ends, wherein the method comprises:
   hydrolyzing a dichlorosilane compound represented by the following formula (1)

Cl—Z—R$^1$—R$_f$—R$^1$—Z—Cl     (1)

wherein R$_f$ is a divalent fluorinated polyether group, R$^1$ may be the same with or different from each other and is a substituted or unsubstituted divalent hydrocarbon group which may have at least one atom selected from the group consisting of oxygen, nitrogen, silicon, and sulfur atoms, and Z is a group represented by the following formula (2)

—SiR$^2$R$^3$—     (2)

wherein R$^2$ and R$^3$ may be the same with or different from each other and are monovalent organic groups in the presence of a tertiary amine compound and a solvent comprising a fluorinated solvent; and
   storing the disilanol compound in the presence of the tertiary amine having a boiling point of 100° C. or higher, said disilanol compound being obtained by the hydrolysis.

2. The method according to claim , wherein the tertiary amine compound is represented by the following formula (4)

R$^4$—[N(R$^5$)-Q]$_a$-R$^6$     (4)

wherein R$^4$ is a C$_{1-20}$ monovalent hydrocarbon group which may have an ether bond, R$^5$ may be the same with or different from each other and is a C$_{1-20}$ monovalent hydrocarbon group which may have an ether bond, R$^6$ is a hydrogen atom or a $C_{1-20}$ monovalent hydrocarbon group which may have an ether bond, at least two of $R^4$, $R^5$ and $R^6$ may be bonded together to form a ring structure, Q may be the same with or different from each other and is a $C_{1-20}$ divalent hydrocarbon group which may have an ether bond, and a is an integer of from 1 to 10.

3. The method according to claim 1, wherein the tertiary amine compound is at least one selected from the group consisting of triethylamine, tripropylamine, tributylamine, trihexylamine, trioctylamine, tetraethylethylenediamine, pentaethyldiethylenetriamine, hexamethyltriethylenetetramine, 1,4-dimethylpyperadine, N-methylmorphorine, 1-azabicyclo[2,2,2]octane, 1,4-dazabicyclo[2,2,2]octane, and N,N-dimethylaniline.

4. The method according to claim 3, wherein the tertiary amine compound is a mixture of triethylamine and tri-n-butylamine.

5. The method according to claim 1, wherein the tertiary amine compound is present in such an amount that a molar ratio of the tertiary amine to the Si—Cl bond in the compound represented by the formula (1) is at least 0.1.

6. The method according to claim 5, wherein the tertiary amine compound is present in such an amount that a molar ratio of the tertiary amine to the Si—Cl bond in the compound represented by the formula (1) ranges from 2 to 50.

7. The method according to claim 1, wherein the method further comprises the step of adding a carbonate salt or a hydrogen carbonate salt of an alkali metal and/or alkali earth metal, or a mixture thereof to the hydrolysis reaction mixture resulting from the step of the hydrolysis.

8. The method according to claim 1, wherein the tertiary amine having a boiling point of 100° C. or higher is selected from a group consisting of tripropylamine, tributylamine, trihexylamine and trioctylamine.

9. The method according to claim 1, wherein the fluorinated solvent comprises at least one selected from the group consisting of trifluorobenzene, 1,3-bistrifluoromethylbenzene and fluoroalkyl ether.

10. The method according to claim 1, wherein the tertiary amine compound having a boiling point of 100° C. or higher is selected from the group consisting of tripropylamine, tributylamine, trihexylamine and trioctylamine.

11. The method according to claim 1, wherein the tertiary amine compound having a boiling point of 100° C. or higher is selected from the group consisting of tributylamine and trioctylamine.

12. The method of claim 1, wherein said tertiary amine compound used in said hydrolyzing step comprises a low boiling point tertiary amine having a boiling point of 100° C. or lower.

13. The method of claim 1, wherein said high boiling point tertiary amine is also used in said hydrolyzing step.

* * * * *